US00PP22337P2

(12) United States Plant Patent
Kobayashi

(10) Patent No.: US PP22,337 P2
(45) Date of Patent: Dec. 13, 2011

(54) POINSETTIA PLANT NAMED 'PER3809A'

(50) Latin Name: *Euphorbia pulcherrima Willd.*
Varietal Denomination: PER3809A

(75) Inventor: Ruth Kobayashi, Carlsbad, CA (US)

(73) Assignee: The Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 13/134,377

(22) Filed: Jun. 6, 2011

(51) Int. Cl.
*A01H 5/00* (2006.01)

(52) U.S. Cl. ..... Plt./306

(58) Field of Classification Search ..... Plt./306
See application file for complete search history.

(56) References Cited

U.S. PATENT DOCUMENTS

| | | | | |
|---|---|---|---|---|
| PP8,817 | P * | 7/1994 | Fruehwirth | Plt./306 |
| PP18,866 | P3 * | 6/2008 | Zerr | Plt./306 |
| PP20,404 | P2 * | 10/2009 | Kobayashi | Plt./306 |

* cited by examiner

*Primary Examiner* — Wendy C Haas
(74) *Attorney, Agent, or Firm* — C. A. Whealy

(57) ABSTRACT

A new and distinct cultivar of Poinsettia plant named 'PER3809A', characterized by its compact, uniform, upright and mounded plant habit; vigorous growth habit; freely branching habit; medium green-colored leaves; mid-season flowering response; large inflorescences with pink-colored flower bracts; and good post-production longevity.

1 Drawing Sheet

Botanical designation: *Euphorbia pulcherrima* Willd.
Cultivar denomination: 'PER3809A'.

BACKGROUND OF THE INVENTION

The present invention relates to a new and distinct cultivar of Poinsettia plant, botanically known as *Euphorbia pulcherrima* Willd., and hereinafter referred to by the name 'PER3809A'.

The new Poinsettia is a naturally-occurring whole plant mutation of *Euphorbia pulcherrima* Willd. 'Eckalbert', disclosed in U.S. Plant patent application Ser. No. 10/291,043, abandoned. The new Poinsettia plant was discovered and selected by the Inventor as a single flowering plant from within a population of plants of 'Eckalbert' in a controlled greenhouse environment in Encinitas, Calif. in July, 2008.

Asexual reproduction of the new Poinsettia plant by terminal vegetative cuttings in a controlled greenhouse environment in Encinitas, Calif. since January, 2009 has shown that the unique features of this new Poinsettia plant are stable and reproduced true to type in successive generations of asexual reproduction.

SUMMARY OF THE INVENTION

Plants of the new Poinsettia have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER3809A'. These characteristics in combination distinguish 'PER3809A' as a new and distinct Poinsettia plant:

1. Compact, uniform, upright and mounded plant habit.
2. Vigorous growth habit.
3. Freely branching habit.
4. Medium green-colored leaves.

5. Mid-season flowering response; under natural season conditions, plants flower in late November in Southern California.
6. Large inflorescences with pink-colored flower bracts.
7. Good post-production longevity.

In side-by-side comparisons conducted in Encinitas, Calif., plants of the new Poinsettia differ primarily from plants of the parent, 'Eckalbert' in plant habit as plants of the new Poinsettia are more compact than plants of 'Eckalbert'.

Plants of the new Poinsettia can be compared to plants of the *Euphorbia pulcherrima* Willd. '490 Pink', disclosed in U.S. Plant Pat. No. 8,817. In side-by-side comparisons conducted in Encinitas, Calif., plants of the new Poinsettia differed primarily from plants of '490 Pink' in the following characteristics:

1. Plants of the new Poinsettia had lighter green-colored leaves than plants of '490 Pink'.
2. Plants of the new Poinsettia and '490 Pink' differed in flower bract color as flower bracts of plants of '490 Pink' were more bluish pink in color.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER3809A' grown in a container.

The photograph at the top of the sheet is a close-up view of a typical inflorescence of 'PER3809A'.

DETAILED BOTANICAL DESCRIPTION

Plants used in the aforementioned photographs and in the following description were grown during the winter in 15-cm containers in a polyethylene-covered greenhouse in Encinitas, Calif. and under natural season conditions and cultural practices which approximate those generally used in commercial Poinsettia production. During the production of the plants, day temperatures averaged 24° C., night temperatures averaged 19° C. and light levels averaged 4,000 foot-candles. Measurements and numerical values represent averages for typical flowering plants. Plants were pinched one time and were 18 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER3809A'.

Parentage: Naturally-occurring whole plant mutation of *Euphorbia pulcherrima* Willd. 'Eckalbert', disclosed in U.S. Plant patent application Ser. No. 10/291,043, abandoned.

Propagation:

*Type.*—Terminal vegetative cuttings.

*Time to initiate roots.*—About seven to ten days at 20° C. night temperature and 27° C. day temperature.

*Time to produce a rooted young plant.*—About four weeks at 20° C. night temperature and 27° C. day temperature.

*Root description.*—Fibrous; white in color.

Plant description:

*Plant habit and form.*—Compact, uniform, upright and mounded plant habit; inverted triangle; large inflorescences positioned above the foliar plane; vigorous growth habit.

*Plant height.*—About 25 cm.

*Plant diameter or spread.*—About 36 cm.

*Lateral branch description.*—Quantity: Freely branching habit, about seven lateral branches develop after pinching. Length: About 17 cm. Diameter: About 4 mm. Internode length: About 2 cm. Strength: Strong. Texture: Smooth, glabrous. Color: Close to 146B.

*Foliage description.*—Arrangement: Alternate, simple. Aspect: Flat. Length: About 14.5 cm. Width: About 10 cm. Shape: Elliptical with lobes. Apex: Acuminate. Base: Rounded to attenuate. Margin: Entire with lobes. Venation pattern: Pinnate, arcuate. Texture, upper surface: Smooth, glabrous. Texture, lower surface: Pubescence along the veins. Color: Developing leaves, upper surface: Close to 146A. Developing leaves, lower surface: Close to 146B. Fully expanded leaves, upper surface: Close to N137C; venation, close to 145A. Fully expanded leaves, lower surface: Close to 146A; venation, close to 145B. Petiole: Length: About 3.8 cm. Diameter: About 2 mm. Texture, upper and lower surfaces: Smooth, glabrous. Color, upper and lower surfaces: Close to 146D.

Inflorescence description:

*Inflorescence type and habit.*—Inflorescences are compound corymbs of cyathia with colored flower bracts subtending the cyathia; inflorescences positioned above the foliar plane.

*Quantity of inflorescence*—One inflorescence develops per lateral branch.

*Fragrance.*—None detected.

*Flowering response.*—Mid-season flowering response; under natural season conditions, plants typically flower in late November in Southern California; under artificial long nyctoperiod/short photoperiod conditions, plants flower about 8.5 weeks later.

*Post-production longevity.*—Good post-production longevity; plants of the new Poinsettia maintain good substance and flower bract color for about four weeks under interior conditions; inflorescences persistent.

*Inflorescence size.*—Diameter: About 31 cm. Height (depth): About 5.5 cm to 6.5 cm.

*Flower bracts.*—Quantity per inflorescence: About 14. Length, largest bracts: About 15.8 cm. Width, largest bracts: About 9.8 cm. Shape: Elliptical with lobes. Apex: Acuminate. Base: Obtuse. Margin: Entire or lobed. Texture, upper and lower surfaces: Smooth, glabrous. Aspect: Mostly horizontal. Venation pattern: Pinnate, arcuate. Color: Developing or transitional bracts, upper surface: Close to 180C. Developing or transitional bracts, lower surface: Close to 182C. Fully expanded bracts, upper surface: Close to 51B; venation, close to 51A; color becoming closer to 51C with development. Fully expanded bracts, lower surface: Close to 51D; venation, close to 51D. Bract petiole: Length: About 3.4 cm. Diameter: About 2 mm. Texture, upper and lower surfaces: Smooth, glabrous. Color, upper and lower surfaces: Close to N34C.

*Cyathia.*—Quantity per corymb: About seven to eight. Length: About 1.1 cm. Width: About 6 mm. Shape: Ovoid. Color, immature: Close to 146C. Color, mature: Close to 146B.

*Nectaries.*—Quantity per cyathium: One or two. Length: About 3 mm. Width: About 2 mm. Shape: Elliptical. Color: Close to 17A.

*Peduncles.*—Length: About 3 mm. Diameter: About 3 mm. Strength: Strong. Aspect: Mostly upright. Texture: Smooth, glabrous. Color: Close to 146D.

*Reproductive organs.*—Stamens: Quantity per cyathium: About ten. Filament length: About 2.5 mm. Filament color: Close to 60A. Anther shape: Oval; bi-lobed. Anther length: About 1 mm. Anther color: Close to 12B. Amount of pollen: Scarce. Pollen color: Close to 12B. Pistils: Plants of the new Poinsettia have not been observed to develop pistils. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15° C. to about 35° C.

It is claimed:

1. A new and distinct Poinsettia plant named 'PER3809A' as illustrated and described.

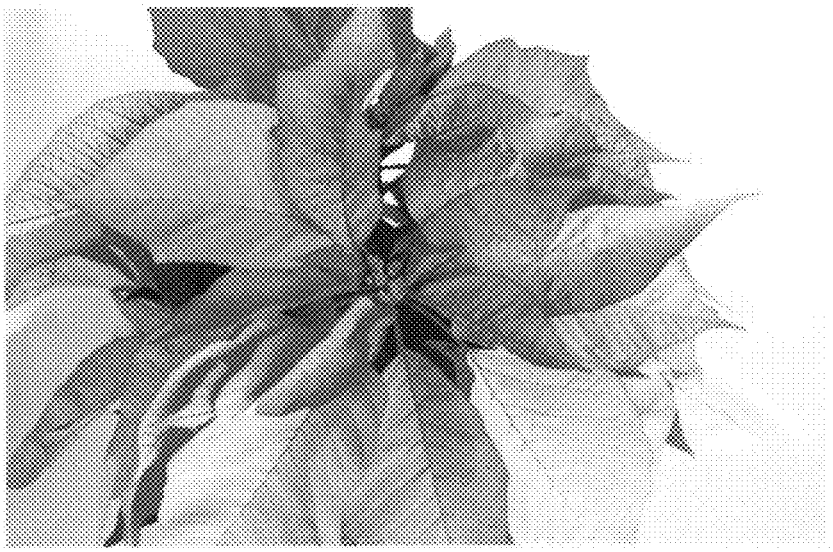
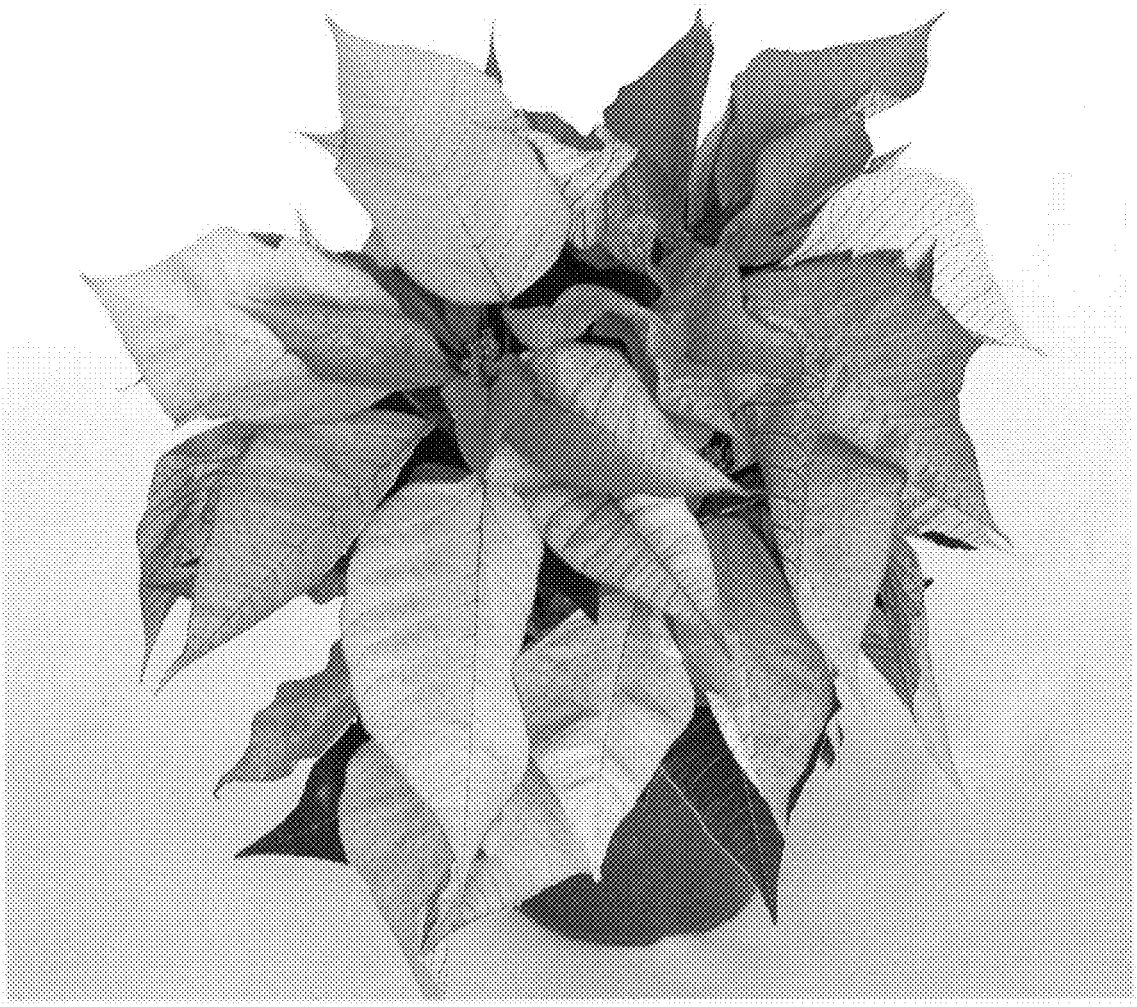

* * * * *